US009422932B2

(12) United States Patent
Petersen et al.

(10) Patent No.: US 9,422,932 B2
(45) Date of Patent: Aug. 23, 2016

(54) ROLLER PUMP WITH DYNAMIC OCCLUSION ADJUSTMENT

(71) Applicant: Medtronic, Inc., Minneapolis, MN (US)

(72) Inventors: Craig Petersen, Brooklyn Park, MN (US); Kartik Radhakrishnan, Brooklyn Park, MN (US); Walter Carpenter, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 764 days.

(21) Appl. No.: 13/668,768

(22) Filed: Nov. 5, 2012

(65) Prior Publication Data

US 2014/0127063 A1 May 8, 2014

(51) Int. Cl.
*F04B 43/12* (2006.01)
(52) U.S. Cl.
CPC ......... *F04B 43/1253* (2013.01); *F04B 43/1276* (2013.01)
(58) Field of Classification Search
CPC ............. F04B 43/1253; F04B 43/1276; F04B 43/1284; F04B 45/08; F17D 1/00; Y10T 137/0318
USPC ........................................... 33/823, 824, 831
See application file for complete search history.

(56) References Cited

U.S. PATENT DOCUMENTS

| 3,628,386 | A | * | 12/1971 | Blum | 74/89.14 |
|---|---|---|---|---|---|
| 4,221,543 | A | | 9/1980 | Cosentino et al. | |
| 4,363,609 | A | | 12/1982 | Cosentino et al. | |
| 4,547,136 | A | * | 10/1985 | Rothstein | 417/475 |
| 4,548,553 | A | * | 10/1985 | Ferster | 417/477.7 |
| 4,568,255 | A | | 2/1986 | Lavender et al. | |
| 5,586,872 | A | | 12/1996 | Skobelev et al. | |
| 5,657,000 | A | * | 8/1997 | Ellingboe | 340/608 |
| 6,036,459 | A | | 3/2000 | Robinson | |
| 6,607,363 | B1 | | 8/2003 | Domroese | |
| 6,736,617 | B2 | | 5/2004 | Domroese | |
| 6,971,143 | B2 | | 12/2005 | Domroese | |
| 2008/0213113 | A1 | | 9/2008 | Lawrence et al. | |
| 2009/0269228 | A1 | | 10/2009 | McIntosh | |

* cited by examiner

*Primary Examiner* — Peter J Bertheaud
*Assistant Examiner* — Dnyanesh Kasture (57) ABSTRACT

A roller pump including a drive shaft, a motor, a roller head assembly, a stator housing, and an occlusion adjustment assembly. The drive shaft is coupled to the motor. The roller head assembly includes a hub, a slide body, and a roller. The hub is mounted to the drive shaft, and maintains the slide body and the roller. The stator housing forms a raceway receiving surface. The occlusion adjustment assembly includes an actuator knob, an actuating structure, and a ground shaft. The actuating structure interfaces with the slide body, and thus the roller, with rotation of the knob. The ground shaft supports the knob and is rotationally isolated from the drive shaft. A user and optionally a control system can adjust occlusion while the pump continuously delivers a fluid medium.

19 Claims, 9 Drawing Sheets

ROLLER PUMP WITH DYNAMIC OCCLUSION ADJUSTMENT

BACKGROUND

The present disclosure relates to roller pumps used in medical devices or systems (e.g., heart-lung bypass machine). More particularly, it relates to roller pumps having occlusion adjustment features that can be actuated during operation of the pump.

Roller (or peristaltic) pumps have many uses in the medical field. For example, roller pumps are used during cardiovascular surgery to facilitate circulation of blood between a patient and a heart-lung machine. The operation of a roller pump is to pump fluid by positive displacement using revolving rollers that occlude flexible tubing. In the context of a heart-lung machine, several dedicated roller pumps are commonly used as part of the perfusion circuit to pump the arterial circuit (where a centrifugal pump is not used), vent, cardiotomy suction, and cardioplegia. Other common medical uses are the transfer of blood between a patient and a kidney dialyzer, and intravenous (IV) feeding of IV solutions. Generally, roller pumps are simply structured, generate a constant flow, and use disposable tubing through which a fluid medium is transferred.

Roller pumps generally comprise a pump drive and a pump head. The pump drive causes rotation of the pump head to pump a fluid medium. The pump head comprises a pump stator and a pump rotor. The pump stator is essentially a chamber or housing having an inner circumferential surface (or "raceway") against which one or more tubes are compressed by the pump rotor. The pump rotor, which is rotatable relative to the stator, is arranged in the pump stator in such a manner that the pump rotor engages tubing positioned in the pump stator with one or more rollers. Upon rotation of the pump rotor by a rotating shaft that is otherwise part of the pump drive, the roller(s) compress the tubing against the inner circumferential surface of the pump stator as it is rolled along the tubing. The fluid medium contained in the tubing is then transported in a direction of the pump rotor rotation.

It is important that roller pumps be adjustable. One way that rotor pumps are generally adjustable is with respect to the rate of rotation of the rotor, including the rollers. Most roller pumps have controls that allow a user to adjust and/or set the rotation rate. Another way that roller pumps are generally adjustable is with respect to the distance between the rollers and the inner circumferential surface of the stator. This parameter is often referred to as "occlusion" and reflects the degree to which the tubing is compressed or occluded between the rollers and the raceway surface. The degree or level of occlusion increases as the rollers are moved into closer proximity with the raceway surface. Varying the amount the rollers occlude or compress the diameter of the tubing in the pump as they move affects the pumping rate. The level of occlusion of the tubing also affects the amount of suction on the fluid medium. If the roller pump is used in certain portions of the anatomy, there may be limits on the amount of suction that can be applied safely to withdraw a fluid medium. An example of such a use for a roller pump is connected to a heart vent line, where too much suction could result in tissue damage. Additionally, the distance between the rollers and the raceway may be adjusted to accommodate differentially-sized (or quality) tubing. In summary, a perfusionist often desires to adjust occlusion to optimize competing criteria such as blood hemolysis, tubing spatulation, flow rate calculation accuracy, and to compensate for manufacturing variations in tubing.

Conventional perfusion roller pumps typically incorporate an occlusion adjustment mechanism that allows the perfusionist to manually adjust the occlusion "setting" or level. Known occlusion adjustment mechanisms are relatively simplistic, and require that the pump drive be deactivated (i.e., the roller pump is not pumping fluid) while the occlusion setting is adjusted. While viable, this approach can be quite time consuming and requires that the pump be stopped every time the perfusionist wishes to adjust occlusion. Moreover, occlusion adjustment typically requires the perfusionist to adjust the distance between the rollers and the raceway with one hand while holding a piece of tubing filled with a column of liquid at a height of one meter above the pump head with the other hand and determine when the column of liquid is dropping at a rate of 2.5 centimeters per minute. This is both cumbersome and inconsistent.

In light of the above, a need exists for roller pumps, especially roller pumps used in perfusion circuits, providing improved occlusion adjustment features.

SUMMARY

Some aspects in accordance with principles of the present disclosure relate to a roller pump including a drive shaft, a motor, a rotor assembly, a stator housing, and an occlusion adjustment assembly. The drive shaft defines a central axis and is coupled to the motor. The motor thus rotates the drive shaft about the central axis. The rotor assembly includes a hub, a slide body, and a roller. The hub is mounted to the drive shaft. The slide body is slidably connected to the hub such that the slide body rotates with rotation of the hub, but can be moved radially relative to the hub. The roller is rotatably coupled to the slide body opposite the drive shaft. The stator housing forms a raceway having an inner arcuate receiving surface. In this regard, the stator housing is associated with the rotor assembly to define an occlusion zone between the roller and the receiving surface. The occlusion adjustment assembly slidably adjusts a radial position of the roller relative to the receiving surface, and includes an actuator knob, an actuating structure, and a ground shaft. The actuating structure is connected to the knob. The ground shaft supports the actuator knob relative to the drive shaft. In this regard, the actuating structure interfaces with the slide body to selectively alter a radial position of the slide body relative to the central axis of the drive shaft (and thus relative to the receiving surface) with rotation of the knob. Finally, the drive shaft and the ground shaft are rotationally isolated from one another. With this construction, roller pumps of the present disclosure allow a user to perform occlusion adjustment while the pump is otherwise operating to pump a fluid medium. In some embodiments, the occlusion adjustment assembly further includes a ring threadably coupled to the knob and longitudinally affixed to the cam structure such that rotation of the knob is translated to longitudinal movement of the cam structure via the ring. In yet other embodiments, an occlusion shaft is co-axially disposed within a lumen of the ground shaft, with an end portion of the occlusion shaft extending beyond the ground shaft and acted upon by a cartridge motor operable to effectuate occlusion adjustment via an electronic controller. In related embodiments, the controller is programmed to prompt operation of the cartridge motor based on a perfusion circuit parameter such as line pressure, motor torque, flow rate and/or user input.

Other embodiments in accordance with principles of the present disclosure relate to a method operating a roller pump as part of a perfusion circuit. The method includes loading a tubing line of the perfusion circuit to the roller pump described above, with the tubing line being disposed against the raceway receiving surface. The motor is operated to cause the slide body and roller to rotate relative to the so-loaded tubing line to effectuate pumping of a fluid medium through the tubing line. In this regard, the roller is located at a first radial position relative to the receiving surface, thereby occluding the tubing line at a first level of occlusion. While continuing to operate the motor, the actuator knob is rotated to alter a radial location of the roller to a second radial position differing from the first radial position so as to provide a second level of occlusion. In some embodiments, the roller pump further includes a cartridge motor linked to the occlusion adjustment assembly, and a controller programmed to prompt operation of the cartridge motor. In these embodiments, the method can further include receiving information at the controller indicative of an operating parameter of the perfusion circuit. The controller automatically prompts operation of the cartridge motor to effectuate movement of the roller to a third radial position relative to the receiving surface as a function of the received information with continuous operation of the motor.

DETAILED DESCRIPTION

Figure 1:
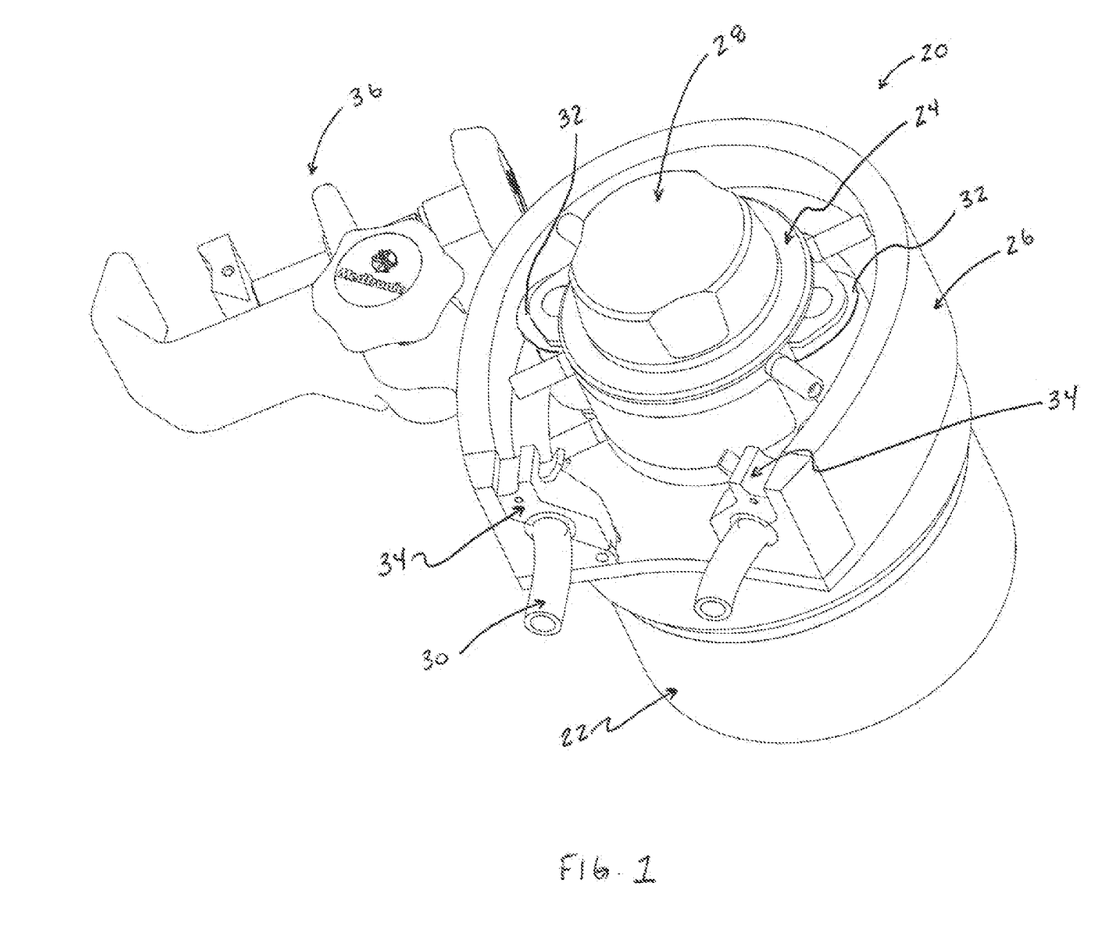
FIG. 1 is a perspective view of a roller pump in accordance with principles of the present disclosure.

One embodiment of a roller pump 20 in accordance with principles of the present disclosure is shown in FIG. 1. The roller pump 20 includes a housing 22 maintaining various drive components (not shown, but described in greater detail below), a roller head assembly 24, a stator frame 26, and an occlusion adjustment assembly 28 (referenced generally). Details on the various components are provided below. In general terms, the roller pump 20 is configured to maintain a length of flexible tubing 30 between the stator frame 26 and one or more rollers 32 provided with the roller head assembly 24. Optionally, one or more tubing clamps 34 can be provided to retain the tubing 30 as desired. Regardless, the tubing 30 is pressed between the stator frame 26 and the roller(s) 32. With rotation of the roller head assembly 24 (via the drive components within the housing 22), the roller(s) 32 travels along the tubing 30, thereby pushing a fluid medium through the tubing 30. A radial position of the roller(s) 32 relative to the stator frame 26 is adjustable via operation of the occlusion adjustment assembly 28. In this regard, the occlusion adjustment assembly 28 is configured such that occlusion adjustment (i.e., changing the level or degree of occlusion) can be performed while the roller head assembly 24 continues to rotate (and thus while the roller pump 20 continues to pump fluid). The roller pump 20 can optionally include other features, such as the auxiliary mounting assembly 36 as shown (the optional auxiliary mounting assembly 36 is omitted from the remaining views).

Figure 2:
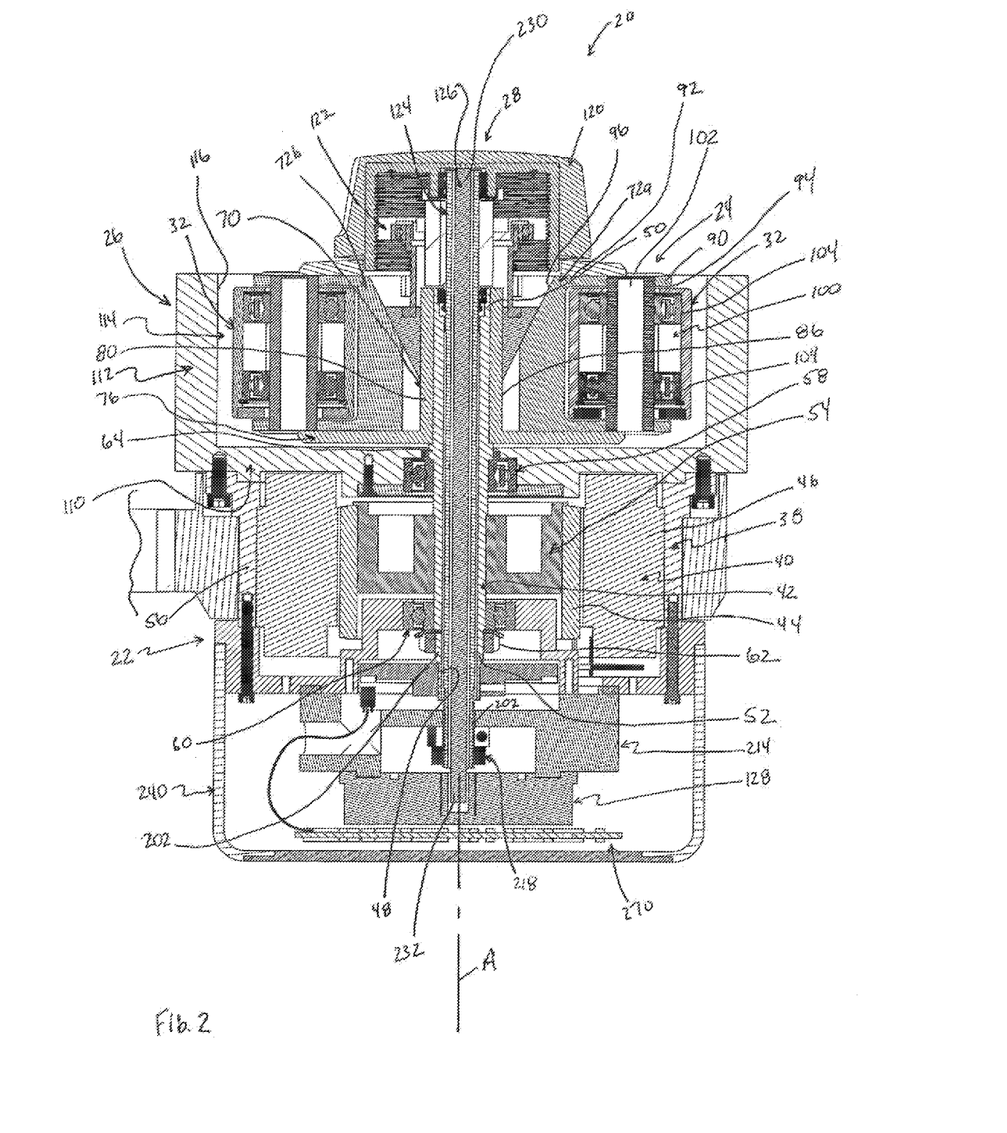
FIG. 2 is a longitudinal cross-sectional view of the roller pump of FIG. 1.

Components of a drive assembly 38 maintained by the housing 22 are shown in FIG. 2 and include a motor 40 and a drive shaft 42. The motor 40 can assume various forms, for example a DC brushless and frameless motor including a rotor 44 and a stator 46. The drive shaft 42 is coupled to the motor 40 such that operation of the motor 40 causes the drive shaft 42 to rotate about a central axis A. The drive shaft 42 can be an elongated, rigid tube forming a central passageway or lumen 48 that is otherwise open at opposing first and second ends 50, 52 of the drive shaft 42. As used throughout this specification, reference to "radial" or "longitudinal" directions is relative to the central axis A.

Driven coupling between the motor 40 and the drive shaft 42 can be effectuated in various manners, for example by a hub 54 that is rigidly connected to the rotor 44 and the drive shaft 42. Further, the drive assembly 38 can include additional features that effectuate stabilized mounting of the motor 40 and the drive shaft 42 relative to other components of the roller pump 20 (e.g., the stator frame 26 and the roller head assembly 24). For example, the housing 22 can include or define a motor housing section 56 that at least partially encloses the motor 40. Upper and lower main bearing units 58, 60 rotatably support the drive shaft 42. In some embodiments, a locking nut 62 is mounted to the drive shaft 42 adjacent the lower main bearing unit 60, and a flange 64 is formed by the drive shaft 42 at the upper main bearing unit 58 to limit overt longitudinal movement of the drive shaft 42.

Figure 3:
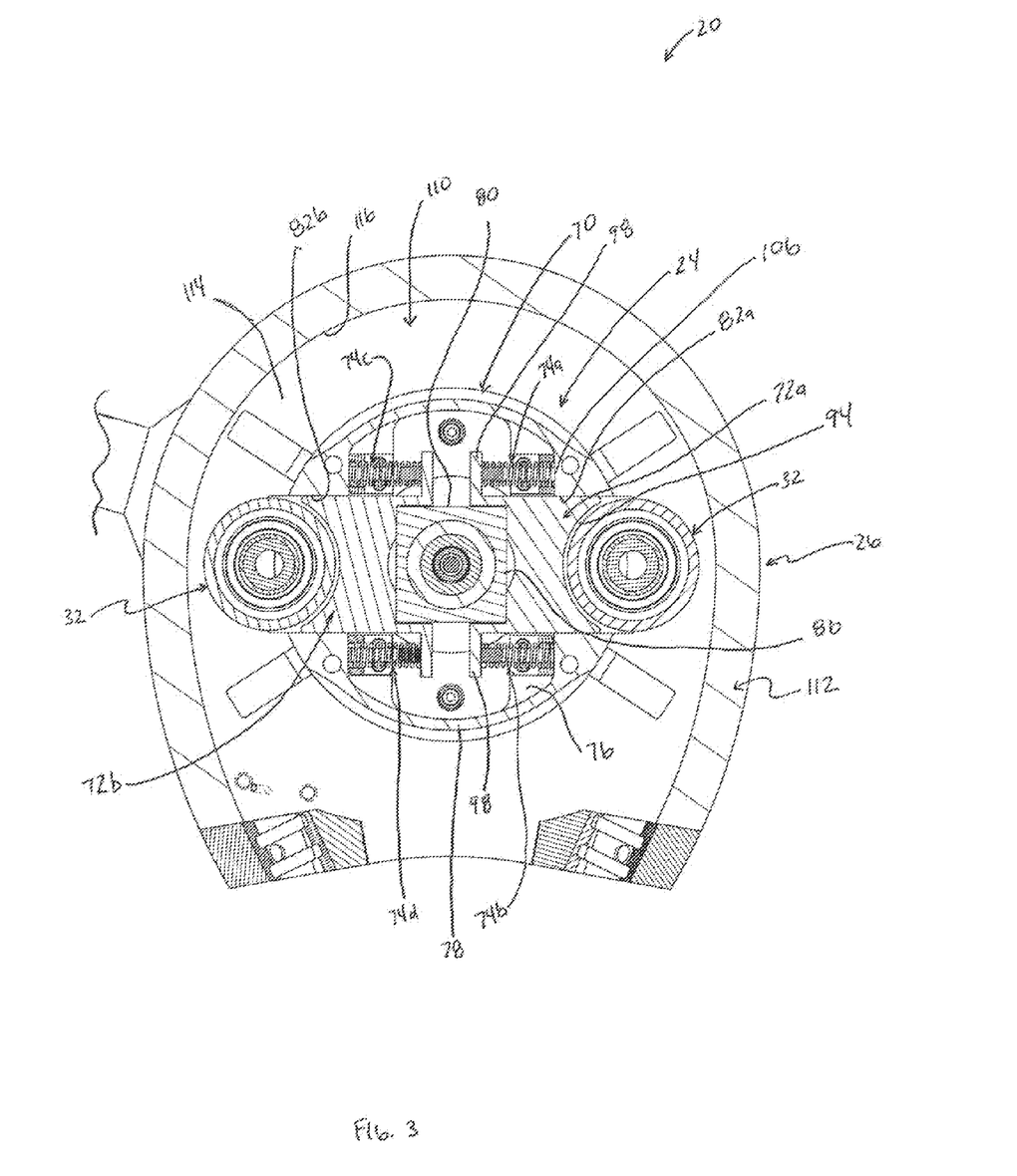
FIG. 3 is a transverse cross-sectional view of the roller pump of FIG. 1.
Figure 4:
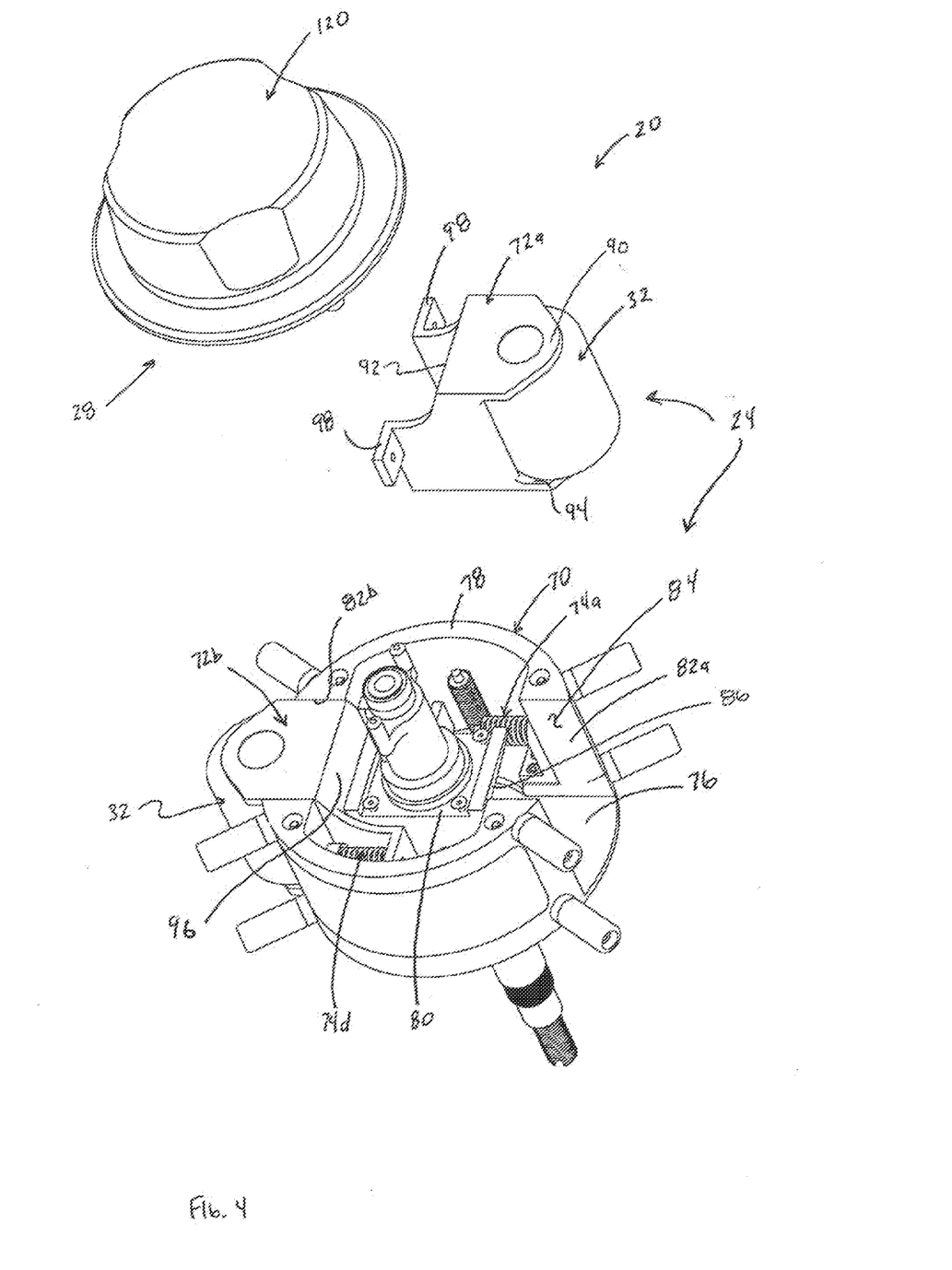
FIG. 4 is an exploded, perspective view of the roller pump of FIG. 1.

With reference to FIGS. 2-4, the roller head assembly 24 includes, in some constructions, a hub 70, one or more slide bodies 72a, 72b, one or more of the rollers 32, and one or more optional biasing devices (e.g., springs) 74a-74d. The hub 70 is a generally cylindrical body defining a base wall 76, an outer wall 78 and a central post 80. One or more slots 82a, 82b are formed through a radial thickness of the outer wall 78 and are sized to slidably receive a respective one of the slide bodies 72a, 72b. More particularly, the base wall 76 slidably supports the slide bodies 72a, 72b, and opposing side surfaces 84 (one of which is fully visible in FIG. 4) defining the corresponding slot 82a, 82b bear against a side of the corresponding slide body 72a, 72b to transfer rotational movement of the hub 70 onto the slide bodies 72a, 72b. Finally, the central post 80 is configured for mounting to the drive shaft 42 adjacent the first end 50 and defines a guide face 86.

While the roller pump 20 is illustrated as including two of the slide bodies 72a, 72b, any other number, greater or lesser, is also acceptable. With the one embodiment shown, the slide bodies 72a, 72b are identical, such that the following description of the first slide body 72a applies equally to the second slide body 72b. As shown in FIG. 3, the slide body 72a defines a leading side 90 and a trailing side 92. A cutout 94 is formed at the leading side 90, and is sized and shaped to rotatably maintain one of the rollers 32. The trailing side 92 forms a receiving face 96 (best shown in FIG. 2 and for the second slide body 72b in FIG. 4) configured to slidably interface with a corresponding component of the occlusion adjustment assembly 28 as described below. Finally, the slide body 72a can include various features that facilitate assembly with corresponding ones of the springs 74a-74d. For example, the slide body 72a can include opposing fingers 98 projecting from the trailing side 92 and configured for attachment to an end of one of the springs 74a-74d.

Each of the slide bodies 72a, 72b rotatably maintains one of the rollers 32. In this regard, and as identified for the roller 32 associated with the first slide body 72a in FIG. 2, the roller 32 can be provided as part of a roller sub-assembly 100 that otherwise includes a pin 102 and roller bearing units 104. The roller bearing units 104 rotatably connect the roller 32 with the pin 102. Further, the pin 102 is configured for assembly to the leading side 90 of the slide body 72a. With this construction, then, the slide body 72a maintains the corresponding roller 32 at a fixed radial location relative to the trailing side 92, and in particular the receiving face 96, such that the roller 32 moves radially relative to the central axis A with radial sliding movement of the slide body 72a. Further, rotation of the hub 70 (via rotation of the drive shaft 42) is transferred to the slide body 72a, 72b, and thus to the corresponding rollers 32.

As best shown in FIG. 3, the springs 74a-74d can be identical, and are provided in pairs with a corresponding one of the slide bodies 72a-72b. Two of the springs 74a, 74b are assembled between the first slide body 72a and the outer wall 78. In particular, a first end of each of the springs 74a, 74b is coupled to a respective one of the slide body fingers 98, and an opposing, second end of each spring 74a, 74b is mounted to an interior face 106 of the outer wall 78. With this construction, the springs 74a-74d preload the slide bodies 72a, 72b toward the central axis A for reasons made clear below.

As best shown in FIGS. 2 and 3, the stator frame 26 includes, in some embodiments, a base 110 and a flange portion 112. The base 110 is sized and shaped to generally match a size and shape of the outer housing 22, and is configured for assembly to the motor housing section 56. The flange 112 extends from the base 110 to define a raceway 114 having an inner arcuate receiving surface 116 against which the flexible tubing 30 (FIG. 1) is disposed as described below.

With reference to FIG. 2, occlusion adjustment assembly 28 includes, in some embodiments, an actuator knob 120, an actuating structure 122, a ground shaft 124, and an optional occlusion shaft 126. In general terms, the actuating structure 122 is connected with the knob 120 such that rotation of the knob 120 effectuates movement the actuating structure 122. Further, the actuating structure 122 interfaces with the slide bodies 72a, 72b so as to adjust a radial position of the slide bodies 72a, 72b. The ground shaft 124 is rigidly connected to the motor housing 56 (or other "ground" component that keeps the ground shaft 124 stationary) and supports the knob 120 relative to the drive shaft 42 and the roller head assembly 24 in a manner rotationally isolating the knob 120 from the roller head assembly 24/drive shaft 42. The occlusion shaft 126 is rigidly connected to the knob 120 and thus turns with rotation of the knob 120 (and vice-versa). As described below, the occlusion shaft 126 couples the knob 120 to an optional occlusion cartridge motor 128.

Figure 5A:
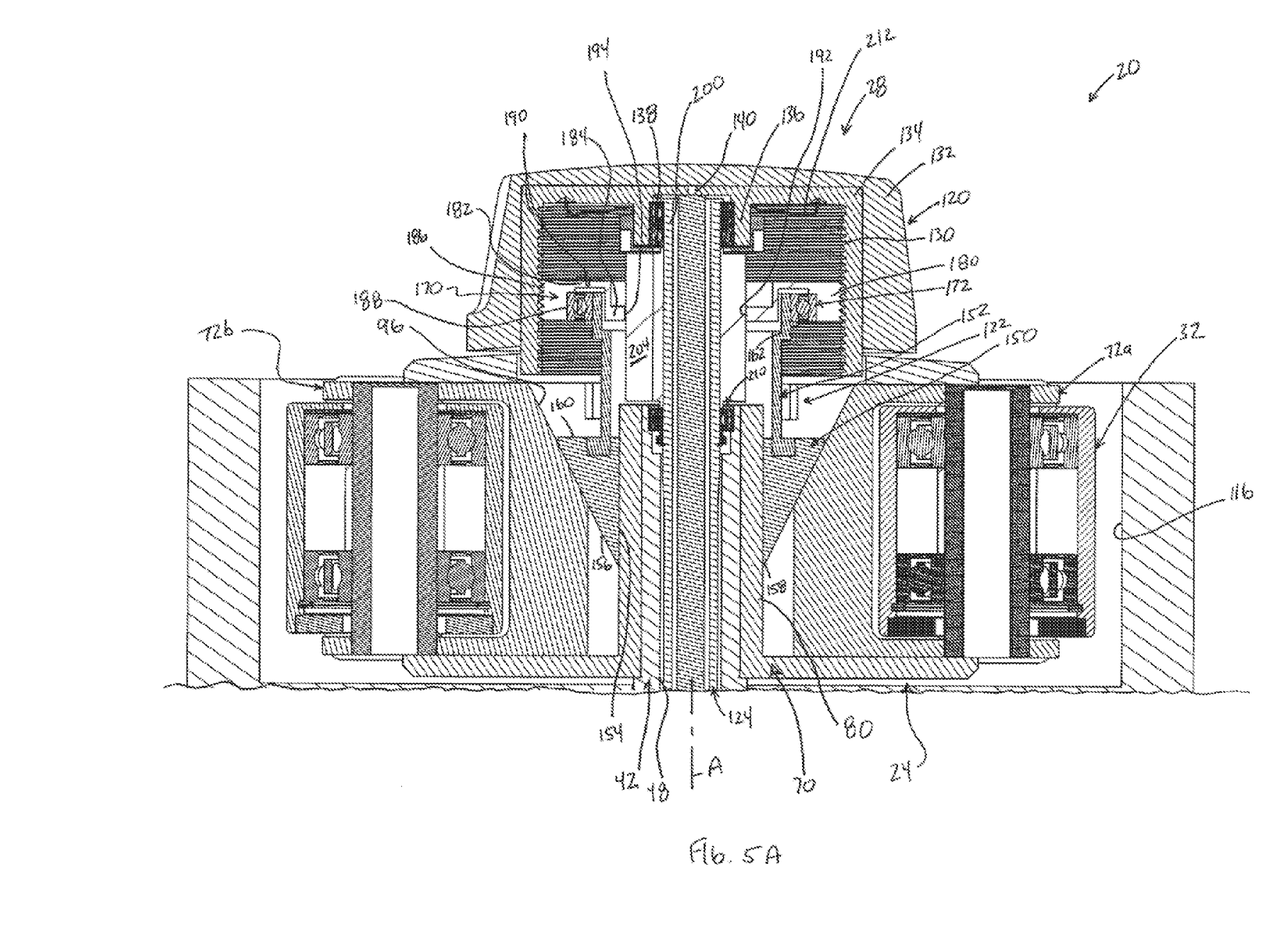
FIG. 5A is an enlarged view of a portion of the roller pump of FIG. 2.

Portions of the occlusion adjustment assembly 28 are shown in greater detail in FIG. 5A. As illustrated, in some embodiments, the knob 120 forms or includes internal threads 130, and can be constructed of two or more components, such as a plastic cap 132 over molded to a threaded insert 134. With this approach, the molded cap 132 can define various exterior surface features that facilitate ergonomic grasping or handling by a user. Conversely, the threaded insert 134 can be formed of a metal or other structurally robust material that facilitates precise formation of the internal threads 130. Regardless of an exact construction, one or more features are further provided to facilitate rotationally isolated mounting or connection of the knob 120 with the ground shaft 124. For example, the knob 120 can form a bushing 136 configured for rotatable connection to the ground shaft 124 via one or more actuator bearing units 138 as described below. Finally, a pinned or other fixed connection between the occlusion shaft 126 and the knob 120 can be provided, such as at a bore 140 formed in the threaded insert 134.

The actuating structure 122 can be akin to a cam and includes, in some embodiments, a cam body 150 and a sleeve 152. The cam body 150 is sized and shaped to interface with the slide bodies 72a, 72b, and the sleeve 152 facilitates coupling with the actuator knob 120 (along with other components described below).

In some embodiments, the cam body 150 is a ring having the wedge-like shape as shown. More particularly, the cam body 150 forms or defines a guide surface 154 and a bearing surface 156. The guide surface 154 defines an inner diameter of the cam body 150, and is sized to slidingly abut the guide face 86 (FIG. 4) of the hub 70. The bearing surface 156 extends in an angular fashion from the guide surface 154 at a leading end 158 of the cam body 150. Stated otherwise, the cam body 150 has an increasing radial thickness from the leading end 158 to a trailing end 160, with the bearing surface 156 being substantially flat. As illustrated, the cam body 150 and the slide bodies 72a, 72b are constructed such that upon final assembly, an angle of extension of the slide body receiving face 96 corresponds with that of the cam body bearing surface 156. Upon final assembly, as the cam body 150 is caused to move in a longitudinal direction (relative to the central axis A), the bearing surface 156 slides along the receiving face 96 of the corresponding slide body 72a, 72b. The actuating structure 122 can assume other formats configured to slidably adjust or move the slide bodies 72a, 72b. For example, the cam interface provided by the longitudinally moving wedge body 150 can be replaced with a scissors-type mechanism.

The sleeve 152 can assume various forms commensurate with other components of the occlusion adjustment assembly 28 described below. In general terms, the sleeve 152 is attached to, and extends from, the trailing end 160 of the cam body 150, and forms a shelf 162 or similar structure.

The actuating structure 122 can be connected to the actuator knob 120 in various fashions. In some embodiments, the occlusion adjustment assembly 28 includes a ring 170 and an occlusion bearing unit 172. The ring 170 forms or defines an outer region 180, an intermediate region 182, and an inner region 184. The outer region 180 defines exterior threads 186. The exterior threads 186 correspond with the internal threads 130 of the actuator knob 120 such that the exterior threads 186 threadably engage the internal threads 130. The intermediate region 182 forms a ledge 188 for mounting to the occlusion bearing unit 172, as well as an annular slot 190 sized and shaped for clearance about a portion of the sleeve 152. Finally, the inner region 184 projects radially inwardly from the intermediate region 182, and terminates at an inner diameter 192 of the ring 170. As generally reflected in FIG. 5A, the inner region 184 further forms a radial notch 194 sized to slidably receive a corresponding segment of the ground shaft 124 as described below.

The occlusion bearing unit 172 rotationally connects the actuating structure 122 and the ring 170, and is mounted at the actuating structure shelf 162 and the ring ledge 188. With this construction, rotation of the actuator knob 120 is transferred to the ring 170 at the threaded interface 130/186, and causes the ring 170 to move in a longitudinal direction. This longitudinal movement or force is transferred to the actuating structure 122 via the occlusion bearing unit 172. Thus, the cam body 150 moves longitudinally with rotation of the actuator knob 120. For reasons made clear below, the occlusion bearing unit 172, while establishing a rigid longitudinal connection between the actuating structure 122 and the ring 170, allows the actuating structure 122 to freely rotate relative to the ring 170. In other words, while rotation of the knob 120 effectuates longitudinal (or other) movement of the actuating structure 122, radial movement is de-coupled through the occlusion bearing unit 172

The ground shaft 124 is concentrically arranged with the drive shaft 42 (i.e., upon final assembly, the drive shaft 42 and the ground shaft 124 share the same, common central axis A). With this but one acceptable construction of FIG. 5A, the ground shaft 124 is sized to be disposed co-axially within the lumen 48 of the drive shaft 42. In this regard, the ground shaft 124 defines opposing, first and second end portions 200, 202 (the second end portion 202 shown in FIG. 2). The ground shaft 124 is sized and shaped such that, upon final assembly, the first end portion 200 extends beyond the first end 50 of the drive shaft 42, and the second end portion 202 extends beyond the second end 52. Further, the first end portion 200 forms a radial key 204. The key 204 is sized to be slidably received within the notch 194 of the ring 170. An interface between the key 204 and the notch 194 is such that the ground shaft 124 resists rotation of the ring 170 (where the ground shaft 124 is held stationary) via the notch 194/key 204 interface. However, the key 204 permits the ring 170 to move or slide longitudinally relative to the ground shaft 124. Thus, any rotational force imparted onto the ring 170 with rotation of the knob 120 is offset or resisted by the ground shaft 124. The ring 170/ground shaft 124 interface ensures that rotation of the knob 120 translates into substantially only longitudinal movement of the ring 170.

A secondary bearing unit 210 is mounted between the drive shaft 42 and the ground shaft 124. The secondary bearing unit 210 longitudinally supports the ground shaft 124 relative to the drive shaft 42 in a manner permitting the drive shaft 42 to rotate relative to the ground shaft 124 (and vice-versa). Stated otherwise, the drive shaft 42 and the ground shaft 124 are rotationally isolated from one another.

In some embodiments, the occlusion adjustment assembly 28 further includes one or more components that provide a user with a physical and/or audible indication of the extent of knob rotation. For example, a spring finger 212 can be assembled to the knob 120, and arranged to generate an audible, optionally tactile, "click" or noise with every revolution, or every segment of revolution, of the knob 120. For example, the spring finger 212 can be arranged to generate a tactile "click" at every 7.2 degree of knob rotation. A variety of other arrangements are also acceptable. In some embodiments, the rotation indication generated by the spring finger 212 correlates with a pre-determined amount or level of occlusion adjustment (e.g., 0.0005 inch occlusion adjustment) as described below.

Figure 5B:
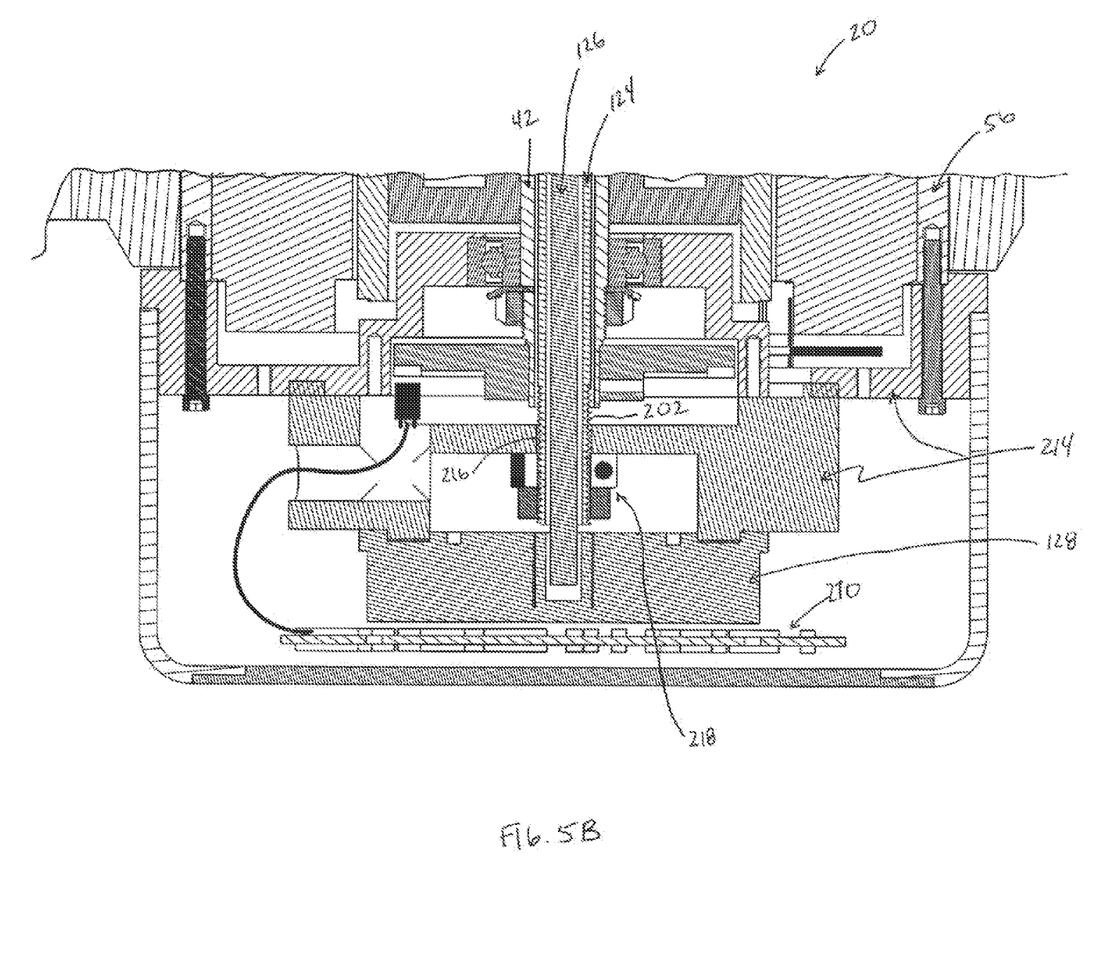
FIG. 5B is an enlarged view of another portion of the roller pump of FIG. 2.

As shown in FIG. 5B, the ground shaft 124 is further supported at the second end portion 202. For example, in some embodiments, intermediate framework 214 is fixed to, and extends from, the motor housing section 56, and provides a threaded surface 216 that threadably engages the second end portion 202. A maximum range of movement between the two components can be limited by a jam nut assembly 218. Other mounting constructions are also envisioned, including those that rigidly retain the ground shaft 124 relative to the motor housing section 56. Regardless, the ground shaft 124 is concentrically maintained relative to the drive shaft 42, and does not longitudinally or rotationally move relative to the motor housing section 56.

Returning to FIG. 2, where provided, the occlusion shaft 126 is concentrically disposed within the ground shaft 124, and defines a first end section 230 and an opposing second end section 232. The first end section 230 is fixed to the knob 120 as described above. Thus, the occlusion shaft 126 effectively serves as an extension of the knob 120. The occlusion shaft 126 has a length sufficient such that the second end section 232 projects beyond the second end portion 202 of the ground shaft 124. The second end section 232 of the occlusion shaft 126 is coupled to the optional cartridge motor 128 with embodiments in which the pump 20 is configured to provide automated occlusion adjustment as described below.

Assembly of the roller pump 20 includes the motor 40 being disposed within the motor housing section 56, and the motor housing section 56 mounted to the stator frame 26. The drive shaft 42 is coupled to the motor 44. The roller head assembly 24, and in particular the hub 70, is mounted to the drive shaft 42. The ground shaft 124 is concentrically arranged within the drive shaft 42, and the cam body 150 placed into an abutting relationship with the hub 70 and the slide bodies 72a, 72b. The actuator knob 120 is connected to the ground shaft 124 in a rotationally isolated fashion. Further, the actuator knob 120 is linked to the actuating structure 122 via the ring 170 (FIG. 5A) and the occlusion bearing unit 172 (FIG. 5A). The motor housing section 56 is mounted to other portions of the housing 22 (e.g., the intermediate framework 214, a bottom cup 240, etc.). Where provided, the occlusion shaft 126 is disposed within the ground shaft 124, linking the knob 120 with the cartridge motor 128. As generally reflected in FIG. 2, upon final assembly, a radial distance between the rollers 32 and the raceway receiving surface 116 is directly related to the radial location of the corresponding slide body 72a, 72b relative to the central axis A. The slide body 72a, 72b radial position, in turn, is dictated by the occlusion adjustment assembly 28, and in particular by a longitudinal arrangement of the cam body 150 (identified in FIG. 5A) as otherwise selected through operation of the knob 120. Notably, the knob 120 is rotationally isolated from the drive shaft 42 for reasons made clear below.

Figure 6:
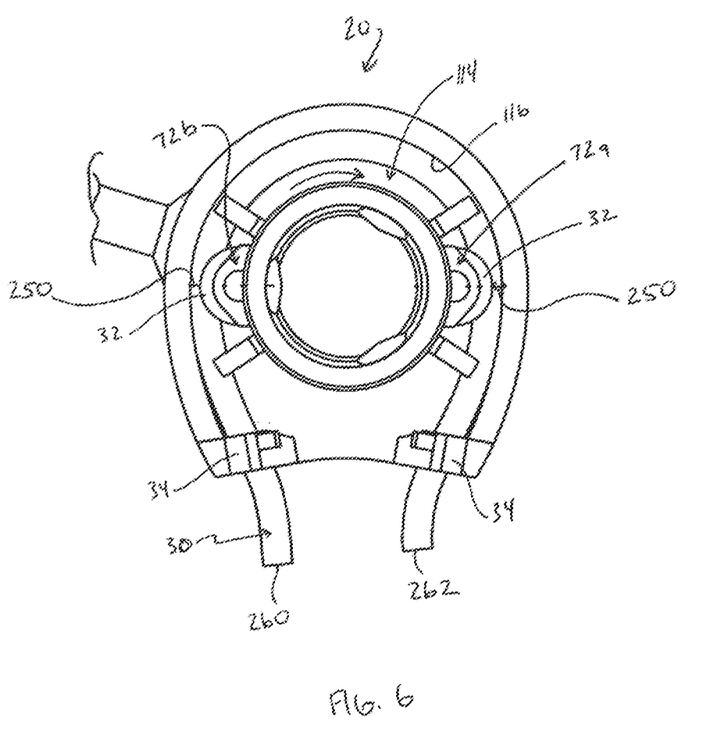
FIG. 6 is a simplified top view of the roller pump of FIG. 1 and illustrating a pumping mode of operation.

During use, the roller pump 20 provides pumping and occlusion adjustment modes of operation, and is useful, for example, as part of a perfusion circuit. Initially, and as shown in FIGS. 1 and 6, a length of the flexible tubing 30 through which the fluid medium is to be pumped is loaded to the roller pump 20. In particular, the tubing 30 is disposed against the receiving surface 116 of the stator raceway 114, and can be held in place by the optional tubing clamps 34. Further, the flexible tubing 30 is pinched against the receiving surface 116 by the rollers 32. In effect, an occlusion zone or distance 250 is established between each of the rollers 32 and the receiving surface 116, with the distance (or "level" of occlusion) 250 being adjustable as described below.

In the pumping mode of operation, and with additional reference to FIG. 2, the motor 40 is operated to rotate the drive shaft 42. Rotation of the drive shaft 42 is transferred to the hub 70, and thus to the slide bodies 72a, 72b and the rollers 32 carried thereby. FIG. 6 reflects the roller head assembly 24 (FIG. 2) rotating in a clockwise direction; as the slide bodies 72a, 72b are caused to rotate relative to the tubing 30, the occlusion zone 250 effectuated by the rollers 32 similarly moves or progresses along the tubing 30 (it being understood that the rollers 32 freely rotate relative to the corresponding slide body 72a, 72b about their axis of symmetry). As a result, a fluid medium is caused to progressively move or "pump" through the tubing 30, with the rotational direction of the roller head assembly 24 effectively establishing a fluid inlet 260 and a fluid outlet 262.

With specific reference to FIG. 5A, rotation of the drive shaft 42/roller head assembly 24 is not transferred to or otherwise imparted upon the ground shaft 124 or the actuator knob 120. That is to say, the knob 120 and the ground shaft 124 are rotationally isolated from the roller head assembly 24 and the drive shaft 42. However, the actuating structure 122 will rotate with rotation of the roller head assembly 24 via the wedged interface of the cam body 150 between the hub 70 and the slide bodies 72a, 72b. The occlusion bearing unit 172 isolates rotational movement of the actuating structure 122 from the ring 170, and thus from the actuator knob 120 and the ground shaft 124. The springs 74a-74d (FIG. 3) maintain a constant pressure between the cam body 150 and the corresponding slide bodies 72a, 72b.

Figure 7:
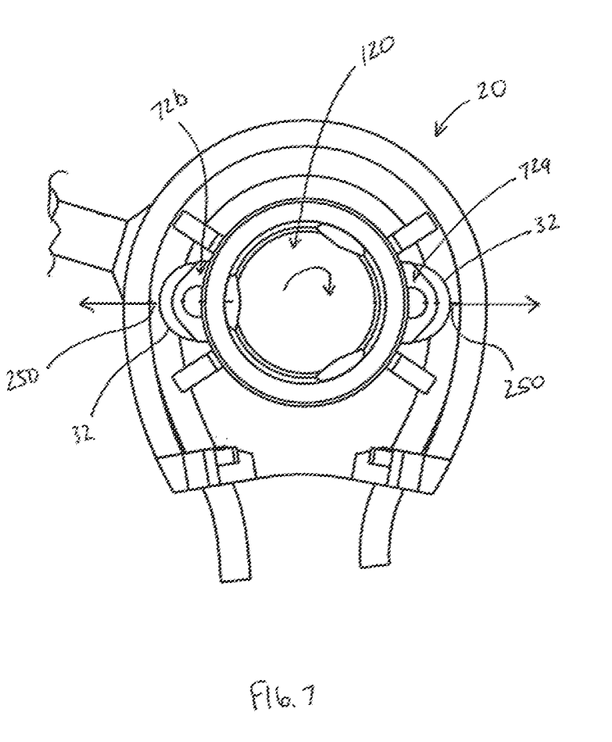
FIG. 7 is a simplified top view of the roller pump of FIG. 1 and illustrating an occlusion adjustment mode of operation.

The level or amount of occlusion (i.e., the radial distance 250 (FIG. 6) between the rollers 32 and raceway receiving surface 116) can be changed in the occlusion adjustment mode of operation. With reference to FIGS. 5A and 7, occlusion adjustment is effectuated by a user rotating the actuator knob 120. Knob rotation is translated into longitudinal movement of the ring 170 via the threaded interface 134, 186. Depending upon the direction of knob rotation, the ring 170 is thus caused to move longitudinally toward or away from the slide bodies 72a, 72b. Due to the longitudinally fixed (but rotationally isolated) connection provided by the occlusion bearing unit 172 between the ring 170 and the cam structure 122 (and in particular the sleeve 152), the actuating structure 122 experiences an identical longitudinal movement with longitudinal movement of the ring 170. Thus, with rotation of the actuator knob 120, the cam body 150 moves longitudinally relative to the slide bodies 72a, 72b. The camming interface between the cam body 150 and the slide bodies 72a, 72b, in turn, affects a change in a radial position of the slide bodies 72a, 72b relative to the central axis A.

As a point of reference, in the view of FIG. 5A, the roller pump 20 is arranged at an intermediate occlusion state, with the ring 170, and thus the cam body 150, at an intermediate longitudinal distance away from the slide bodies 72a, 72b. As reflected in FIG. 7, with rotation of the knob 120 (e.g., clockwise in FIG. 7), the slide bodies 72a, 72b, and thus the rollers 32 carried thereby, are forced radially outwardly, thereby decreasing the occlusion zone or distance 250 associated with each of the rollers 32. With further reference to FIG. 5A, rotation of the knob 120 causes the ring 170, and thus the cam body 150, to move longitudinally toward the slide bodies 72a, 72b (downwardly relative to the orientation of FIG. 5A), with the camming interface between the cam body 150 and the slide bodies 72a, 72b forcing the slide bodies 72a, 72b (and the rollers 32 carried thereby) radially outwardly relative to the central axis A. A maximum occlusion state is achieved once the cam body bearing surface 156 is longitudinally beyond (e.g., below) the slide body receiving surface 96. Rotation of the knob 120 is an opposite direction causes the ring 170, and thus the cam body 150, to move longitudinally away from (upwardly) the slide bodies 72a, 72b. The camming interface force applied by the bearing surface 156 on the receiving surface 96 is thereby reduced. The springs 74a-74d (FIG. 3), in turn, bias the corresponding slide body 72a, 72b radially inwardly. In a minimum occlusion state, the slide bodies 72a, 72b contact the hub post 80.

Any level or amount of occlusion between the minimum occlusion state and the maximum occlusion state can be selected or effectuated by a user. Notably, occlusion adjustment steps can be performed while the roller pump 20 is simultaneously and continuously operating to pump a fluid medium. By rotationally isolating the drive shaft 42 from the actuator knob 120 and the ring 170 via the concentrically arranged ground shaft 124, the roller pump 20 eliminates the need for the user (e.g., perfusionist) to stop the pump every time occlusion adjustment is desired. Commensurate with this explanation, methods of operating a roller pump as part of a perfusion circuit in accordance with principles of the present disclosure include loading the flexible tubing 30 (FIG. 1) to the roller pump 20, operating the motor 40 to cause a fluid medium to be pumped through the tubing 30 with the roller pump 20 arranged at a first level of occlusion, and adjusting the level of occlusion to a second, different level while the motor 40 continues to operate (and the fluid medium continues to be pumped).

In addition to facilitating manual occlusion adjustment, the roller pump 20 optionally further provides for automated occlusion adjustment. For example, FIGS. 2 and 5B illustrates coupling of the optional occlusion shaft 126 with the optional cartridge motor 128. A controller 270 further provides and operates the cartridge motor 128 to selectively rotate the occlusion shaft 126 (and thus the knob 120).

Various mechanisms (not shown) can be employed to effectuate a driven coupling between the cartridge motor 128 and the occlusion shaft 126. For example, a drive gear can be coupled to the occlusion shaft 126, and the cartridge motor 128 operably coupled to the drive gear. With this but one acceptable construction, operation of the cartridge motor 128 causes the drive gear to rotate, that in turn rotates the occlusion shaft 126. Rotation of the occlusion shaft 126 rotates the knob 120 that in turn effectuates a change in the radial position of the slide bodies 72a, 72b as previously described, thus altering the level of occlusion. Other constructions linking the cartridge motor 128 with the knob 120 and/or the cam body 150 are also acceptable.

Figure 8:
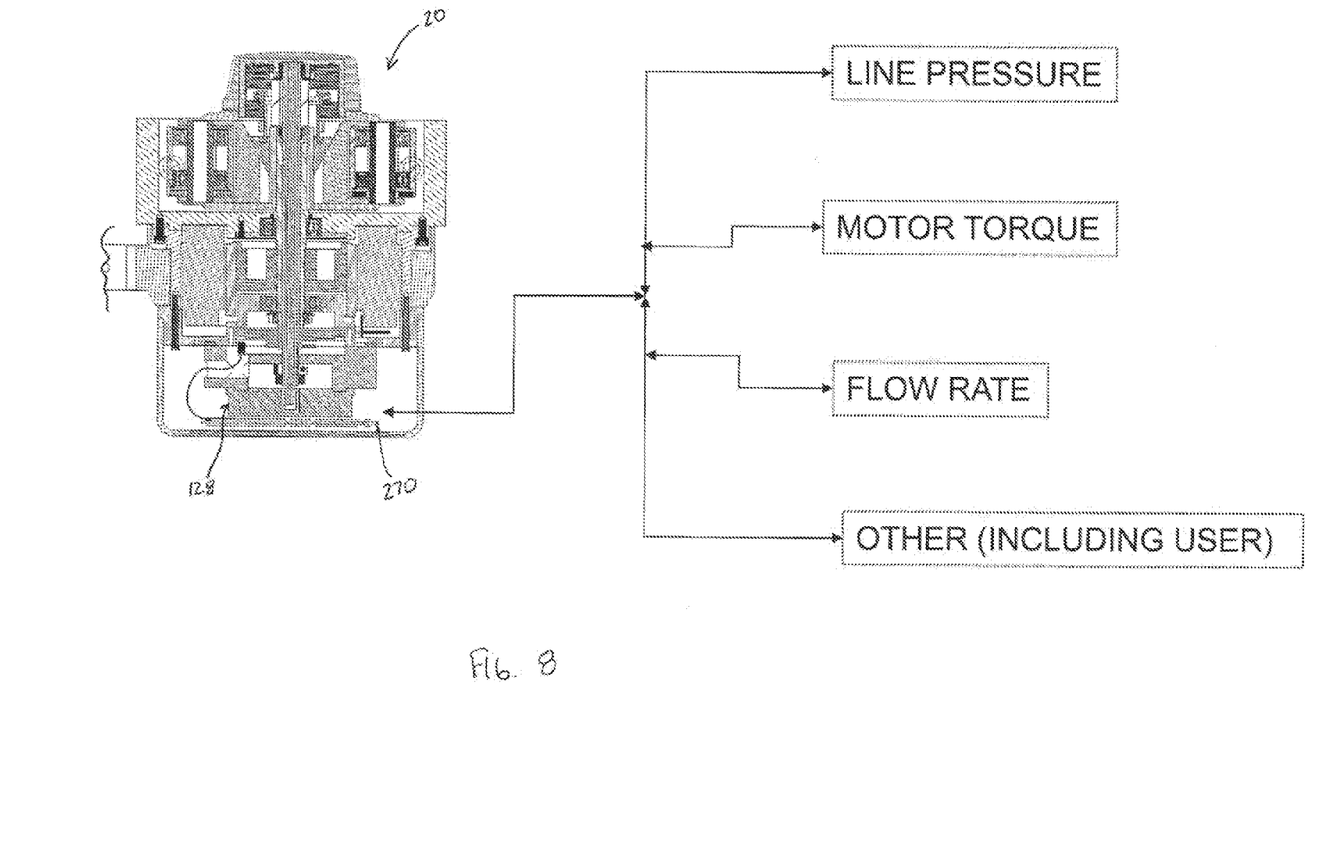
FIG. 8 is a block diagram of a system including the roller pump of FIG. 7.

The controller 270 is or includes a microprocessor or other computer device that is programmed to prompt and control operation of the cartridge motor 128. In this regard, the controller 270 can be programmed to control operation of the cartridge motor 128 as a function of one or more input parameters. For example, the controller 270 can include, or be electronically linked to, an input device (e.g., touch screen) at which a user enters a desired occlusion setting. In related embodiments, other selectable occlusion criteria can be utilized by the controller 252 in determining (and then effectuating) a desired occlusion setting. For example, FIG. 8 provides, in block form, information that can be supplied to the controller 270 from the pumping environment (e.g., a perfusion circuit), based upon which the controller 270 effectuates operation of the cartridge motor 128. For example, input feedback information can include line pressure, motor torque, flow rate, etc. The user/perfusionist can prescribe the occlusion criteria suited for their particular practice. Regardless, as with the manual occlusion adjustment described above, automated occlusion adjustment provided by the roller pump 20 can occur while the pump 20 continues to operate in the pumping mode.

The roller pumps and related methods of use of the present disclosure provide a marked improvement over previous designs. Occlusion adjustment can be performed with continuous operation of the roller pump in pumping a fluid medium. Further, in some embodiments, automated occlusion adjustment is provided.

Although the present disclosure has been described with reference to preferred embodiments, workers skilled in the art will recognize that changes can be made in form and detail without departing from the spirit and scope of the present disclosure.

What is claimed is:
1. A roller pump comprising:
a drive shaft defining a central axis;
a motor coupled to the drive shaft for rotating the drive shaft about the central axis;

a roller head assembly including:
a first hub mounted to the drive shaft,
a first slide body slidably connected to the first hub such that the slide body rotates with rotation of the first hub,
a first roller rotatably coupled to the slide body opposite the drive shaft;
a stator frame forming a raceway having an inner arcuate receiving surface;
wherein the stator frame is associated with the roller head assembly to define an occlusion zone between the roller and the receiving surface; and
an occlusion adjustment assembly for slidably adjusting a radial position of the roller relative to the receiving surface, the occlusion adjustment assembly including:
an actuator knob,
an actuating structure connected to the knob,
a ground shaft disposed within the drive shaft, the ground shaft supporting the actuator knob relative to the drive shaft,
wherein the actuating structure interfaces with the slide body to alter a radial position of the slide body relative to the central axis with rotation of the knob;
wherein the drive shaft and the ground shaft are rotationally isolated from one another.

2. The roller pump of claim 1, wherein the actuator knob is rotationally isolated from the drive shaft.

3. The roller pump of claim 1, when the actuating structure includes a wedge body forming a bearing surface, and further wherein the slide body defines a receiving surface slidably interfacing with the bearing surface.

4. The roller pump of claim 1, wherein the occlusion adjustment assembly further includes a ring coupled to the knob such that the ring moves longitudinally relative to the central axis with rotation of the knob.

5. The roller pump of claim 4, wherein the knob and the ring are threadably coupled to one another.

6. The roller pump of claim 4, wherein the actuating structure is connected to the ring such that longitudinal movement of the ring is transferred to the actuating structure.

7. The roller pump of claim 6, wherein the actuating structure is rotationally isolated from the ring.

8. The roller pump of claim 6, wherein the occlusion adjustment assembly further includes a bearing unit coupled between the actuating structure and the ring.

9. The roller pump of claim 8, wherein the actuating structure includes a wedge body forming a bearing surface slidably interfacing with the slide body, and an intermediate hub extending from the wedge body, further wherein the bearing unit is disposed between the intermediate hub and the ring.

10. The roller pump of claim 1, wherein the ground shaft is arranged co-axially with the drive shaft.

11. The roller pump of claim 10, wherein the occlusion adjustment assembly further includes an actuator bearing unit coupled between the knob and the ground shaft such that the knob is longitudinally fixed relative to the ground shaft and is rotationally isolated from the ground shaft.

12. The roller pump of claim 11, wherein the ground shaft defines opposing, first and second end portions, and further wherein the first end portion extends beyond a first end of the drive shaft, the actuator bearing unit being coupled to the first end portion.

13. The roller pump of claim 12, wherein the second end portion extends beyond an opposing second end of the drive shaft.

14. The roller pump of claim 13, wherein the occlusion adjustment assembly further includes a support device for longitudinally supporting a second end portion relative to the drive shaft.

15. The roller pump of claim 14, wherein the ground shaft extends through a lumen of the drive shaft, and further wherein the support device includes a frame longitudinally fixed relative to the drive shaft, and further wherein the second end portion is coupled to the frame.

16. The roller pump of claim 1, further comprising:
an occlusion shaft fixed to the actuator knob and extending through the ground shaft;
a cartridge motor operably coupled to the occlusion shaft; and
a controller programmed to prompt operation of the cartridge motor.

17. The roller pump of claim 16, wherein the controller is programmed to prompt operation of the cartridge motor as a function of a perfusion circuit parameter selected from the group consisting of line pressure, motor torque, flow rate, and user information.

18. The roller pump of claim 1, wherein the occlusion adjustment assembly further includes a spring finger carried by the knob, and further wherein the spring finger and the knob are configured such that the spring finger generates an audible noise with rotation of the knob relative to the ground shaft.

19. The roller pump of claim 1, wherein the roller head assembly further includes:
a second slide body slidably connected to the first hub; and
a second roller rotatably coupled to the second slide body opposite the drive shaft;
wherein the first and second slide bodies extend from the first hub in opposite directions.

* * * * *